United States Patent [19]

Sun

[11] Patent Number: 4,778,943

[45] Date of Patent: Oct. 18, 1988

[54] SKELETAL ISOMERIZATION OF OLEFINS OVER HALOGEN-CONTAINING ALKALINE EARTH OXIDE CATALYSTS

[75] Inventor: Hsiang-ning Sun, Media, Pa.

[73] Assignee: Atlantic Richfield Company, Los Angeles, Calif.

[21] Appl. No.: 791,044

[22] Filed: Oct. 24, 1985

[51] Int. Cl.$^4$ .............................................. C07C 5/27
[52] U.S. Cl. .................................. 585/671; 585/669; 502/340
[58] Field of Search ................. 585/671, 669; 502/340

[56] References Cited

U.S. PATENT DOCUMENTS 3,558,734  1/1971  Myers ................................. 585/671

FOREIGN PATENT DOCUMENTS 8024350  8/1981  Japan .................................... 585/671
981693  1/1965  United Kingdom ................ 585/669
981964  1/1965  United Kingdom ................ 585/669

*Primary Examiner*—Asok Pal
*Attorney, Agent, or Firm*—Craig E. Larson

[57] ABSTRACT

A process for the skeletal isomerization of olefins wherein the olefins are contacted with a catalyst comprising at least one alkaline earth oxide which has been treated with a halogen compound.

12 Claims, No Drawings

SKELETAL ISOMERIZATION OF OLEFINS OVER HALOGEN-CONTAINING ALKALINE EARTH OXIDE CATALYSTS

BACKGROUND OF THE INVENTION

This invention relates to skeletal isomerization of olefins, i.e., to the reorientation of the molecular structure in respect to the formation or elimination of side chains. This invention more particularly relates to the conversion of unbranched olefins into branched olefins having the same number of carbon atoms.

Skeletal isomerization of olefins is known to be accomplished by contacting unbranched or lightly branched olefins with acidic catalysts at elevated temperatures. The process is generally applicable to the isomerization of olefins having about 4 to about 20 carbon atoms and is especially applicable to olefins having about 4 to about 10 carbon atoms per molecule. The process may be used to form isobutene from normal butenes, methyl pentenes and dimethyl butenes from normal hexenes, and so forth.

Known skeletal isomerization catalysts include aluminas and halogenated aluminas, particularly F- or Cl-promoted aluminas. Supports employed in such catalysts are either alumina or predominantly alumina due mainly to the high acidity of alumina. See Choudary, V. R., "Fluorine Promoted Catalysts: Activity and Surface Properties", *Ind. Eng. Chem., Prod. Res. Dev.*, 16(1), pp. 12–22 (1977) and U.S. Pat. No. 4,400,574.

An object of this invention is an improved process for the skeletal isomerization of olefins, especially for the isomerization of n-butenes to form isobutene. A more specific object is an easily prepared, stable, active and selective isomerization catalyst and process for skeletal isomerization of olefins. Other objects and advantages of the invention will be apparent from the following description.

SUMMARY OF THE INVENTION

A process for the skeletal isomerization of olefins has now been found, which is characterized in that a mixture containing olefins having from about 4 to about 20 carbon atoms per molecule are contacted with a catalyst catalyst comprising at least one alkaline earth oxide which has been treated with a halogen compound. Alkaline earth oxides are oxides of metals selected from the group consisting of Be, Mg, Ca, Sr and Ba. Oxides of Be, Mg and Ca are preferred. Oxides of Mg and Ca are more preferred. Magnesia is particularly preferred. Halogens are selected from the group consisting of F, Cl, Br and I. Treatment of alkaline earth oxides with compounds of Cl and Br is preferred. Particularly preferred are catalysts prepared by contacting magnesia with vapors of Cl and Br compounds.

DETAILED DESCRIPTION OF THE INVENTION

The alkaline earth oxides used as support materials for the catalyst system of this invention can be provided as powders, extrudates, spheres, tablets, pellets or other forms. Preferably, the support will have a surface area of about 50 to about 500 m$^2$/gram (as measured by the BET method using N$_2$). The content of impurities which act to poison isomerization activity, such as alkali metals, should be minimized.

Other inorganic oxides may be used with alkaline earth oxides in the catalyst of this invention. However, the catalyst should contain at least about 50 mole %, preferably at least about 70 mole %, of alkaline earth oxide. Examples of other inorganic oxides which can be used in combination with alkaline earth oxides are alumina, titania, silica, zirconia, thoria, hafnium, oxide, zinc oxide, nickel oxide, phosphorus oxide, boron oxide, lanthamide oxides, gallium oxide, indium oxide, germanium oxide, tin oxide, bismuth oxide, arsenic oxide, molybdenum oxide, tungsten oxide, vanadium oxide and thallium oxide. The alkaline earth oxide and other inorganic oxides may be a physical mixture or may be chemically bonded.

The catalyst is prepared by incorporating from about 0.05 to about 25 wt. % halogen, preferably from about 0.3 to about 10 wt. % halogen, based on the total catalyst weight. Any suitable method of incorporation can be used. For example, the incorporation may be done by impregnating a previously dried and calcined alkaline earth oxide with an aqueous solution of a halogen acid and/or ammonium halide salt.

However, it is preferable to treat the alkaline earth oxide with a gas comprising vapors of halogen sources. Halogen sources are selected from the group consisting of halogen acids, ammonium halide salts, and organic halides. The halogen source selected for this preferred treatment method will be vaporizable under the treatment conditions. Organic halides suitable for use as a halogen source may be either aliphatic or aromatic halides, although aliphatic halides, especially those having from 1 to 4 carbon atoms per molecule, are preparred organic halides. The vapor phase treatment is preferably performed at temperatures within the range of about 100° to about 600° C., more preferably about 250° to about 450° C. The treatment should be performed in a nonoxidizing atmosphere to prevent halide oxidation. Addition of the halogen source in the vapor phase can be either continuous or in pulse. Addition can be effected either before or concurrent with introduction of isomerization feedstock. In one embodiment of this invention, the halogen source is supplied continuously in the isomerization feedstock at a concentration within the range of about 10 to about 5000 ppm (wt., as the halogen, e.g., Br or Cl).

The skeletal isomerization process of this invention is carried out by contacting the feed with the catalyst, using any suitable contacting techniques, at temperatures at which skeletal isomerization of the feed olefins occurs. Feed preferably maintained in the vapor phase during contacting. The temperature is preferably in the range of about 50° to about 800° C., more preferably about 300° to about 450° C. The gas hourly space velocity is not narrowly critical but will generally be within the range of about 10 to about 50,000 hr.$^{-1}$, preferably about 500 to about 10,000 hr.$^{-1}$. Any convenient pressure can be used, with the lowest practical pressure preferred in order to minimize side reactions such as polymerization. Preferred pressures are within the range of about 0.5 to about 300 psia, more preferably about 5 to about 25 psia.

The isomerization feedstock contains at least one alkene, preferably an alkene having from 4 to 12 carbon atoms per molecule, more preferably an alkene having from 4 to 10 carbon atoms per molecule. The alkene may have terminal or internal double bonds. Normal alkenes, especially normal butenes, are preferred feedstocks. Butene feedstocks may contain 1-butene, 2-butene or mixtures thereof. Examples of other normal alkenes which are useful feedstocks are 1- and 2- pentenes; 1-, 2- and 3- hexenes; 1-, 2- and 3- heptenes; and 1-, 2-, 3- and 4-octenes. The normal alkenes can be accompanied by other hydrocarbons, typically other hydrocarbons having the same carbon atoms as the alkene feed. In the case of normal butenes, examples of other hydrocarbons are normal butane and isobutane.

Particular feedstocks contemplated for use in the present process are fractions containing n-butenes, optionally mixed with isobutene, isobutane and n-butane. Such fractions are commonly produced in petrochemical plants and refineries as, for example, after the separation of 1,3- butadiene from a $C_4$ cut or in the cracking of waxy distillates. Isobutene present in such fractions is commonly converted by catalytic reaction with methanol to produce methyl tertiary butyl ether ("MTBE"). MTBE is separated by distillation, leaving a residual $C_4$ cut. Isobutene present in such fractions may also be oligomerized to produce oligomers which are then separated, again leaving a residual $C_4$ cut. In either MTBE production or oligomerization, a mixture of n-butenes, n-butane and isobutane remains in the residual material. It is desirable to produce additional isobutene from the residual material and return the isobutene for further conversion by the reactions mentioned above.

The olefinic feed stream can contain inert gaseous diluents (e.g. paraffins, $N_2$, etc.). The diluent may be present in any desired proportion, e.g., up to about 95 wt. % of the olefinic feed stream.

Selection of isomerization conditions is dependent on olefins to be isomerized. In general, lower temperatures are used for feeds containing larger olefin molecules.

Maintenance of catalyst activity may be enhanced by addition, either continuously or intermittently, of small amounts of a halogen source to the feed stream. Such materials are preferably added to the feed in amounts varying from about 10 to about 10,000 ppm (wt., expressed as the halogen, e.g. Br or Cl), more preferably about 100 to about 1000 ppm.

The catalysts are regeneratable by heating in an oxygen-containing gas at temperatures ranging from about 200° to about 700° C. and treating the oxidized catalyst with a halogen source as described herein.

The invention is further illustrated by reference to the following examples. All performance data reported in the examples were obtained after catalyst stabilization (usually one to three hours after starting the reaction).

EXAMPLE 1

Twenty-five ml. of magnesia was placed in a tubular reactor and treated with a vapor formed by injection of 1 ml. (liquid) of n-butyl bromide into a stream of nitrogen at 430° C. A 1:1 mixture of 1-butene and 2-butenes was passed over the catalyst. At 430° C., 560 GHSV (gas hourly space velocity) and 0 psig, 24.7% conversion of the butene feed was observed. Product selectivities (wt. %) were: 0.1% $C_1$, 0.2% $C_2$, 9.0% $C_3$, 2.8% isobutane/n-butane, 75.5% isobutene, and 12.4% $C_5+$ hydrocarbons.

EXAMPLE 2

Example 1 was repeated except the space velocity was reduced to 280 GHSV. The observed conversion of the butene feed was 38%. Product selectivities (wt. %) were: 0.2% $C_1$, 0.4% $C_2$, 11.1% $C_3$ 3.4% isobutane/n-butane, 68.0% isobutene, and 16.1% $C_5+$ hydrocarbons.

EXAMPLE 3

Twenty-five ml. of MgO obtained by thermal decomposition of magnesium oxalate at 300° C. was placed in a tubular reactor and was treated for 5 minutes with 500 ppm t-butyl chloride in a nitrogen stream. The treated catalyst was contacted with a 1:1 mixture of cis- and trans-2-butenes. At 430° C., 270 GHSV and 755 torr pressure, 37.7% conversion of the butene feed was observed. Product selectivities (wt. %) were: 0.3% C., 0.5% $C_2$, 12.8% $C_3$, 9.4% isobutane, 60.8% isobutene, and 16.3% $C_5+$ hydrocarbons.

EXAMPLE 4

Twenty-five ml. of CaO was placed in a tubular reactor and treated for 10 minutes with 500 ppm. n-butyl bromide in a nitrogen stream. The treated catalyst was contacted with 1-butene. At 450° C., 20 GHSV and 0 psig, 11% conversion was observed. Product selectivities (wt. %) were: 4% $C_1$-$C_3$, 89.1% isobutene, and 6.9% $C_5+$ hydrocarbons.

EXAMPLE 5

Twenty-five ml. of a beryllium oxide obtained by thermal decomposition of beryllium 2,4-pentanedionate was placed in a tubular reactor and treated with a vapor formed by injection of 50 ml of methyl chloride into a stream of nitrogen. The treated catalyst was contacted with 1-butene. At 430° C., 250 GHSV and 745 torr pressure, 29.2% conversion of the butene feed was observed. Product selectivities were: 11% $C_1$-$C_3$, 2.1% isobutane, 76.2% isobutene, and 10.7% $C_5+$ hydrocarbons.

EXAMPLE 6

Twenty-five ml. of a MgO obtained by thermal decomposition of magnesium oxalate at 300° C. was placed in a tubular reactor. The catalyst was contacted with 1-butene feed containing 1000 ppm n-butyl bromide. At 430° C., 325 GHSV and 750 torr pressure, 31.5% conversion of the butene feed was observed. Product selectivities were 9.8% $C_1$-$C_3$, 2.7% isobutane/n-butane, 71.1% isotutene, and 16.5% $C_5+$ hydrocarbons.

What is claimed is:

1. A process for the skeletal isomerization of olefins having from about 4 to about 20 carbon atoms per molecule which comprises contacting said olefins with a catalyst comprising at least one alkaline earth oxide which oxide has been treated with a halogen compound, said catalysts containing at least 70 mole % of said alkaline earth oxide.

2. The process of claim 1 wherein the catalyst comprises magnesia which as been treated with a halogen compound.

3. The process of claim 2 wherein the catalyst is prepared by contacting magnesia with a vapor selected from the group consisting of hydrogen halides, ammonium halides and organic halides.

4. The process of claim 3 wherein the vapor is selected from the group consisting of HCl, NH$_4$Cl and organic chlorides.

5. The process of claim 3 wherein the vapor is selected from the group consisting of HBr, NH$_4$Br and organic bromides.

6. The process of claim 2 wherein a halogen compound is added to the olefin feed during the skeletal isomerization in an amount sufficient to maintain catalyst activity.

7. The process of claim 1 wherein the catalyst comprises calcium oxide which has been treated with a halogen compound.

8. The process of claim 7 wherein the catalyst is prepared by contacting calcium oxides with a vapor selected from the group consisting of hydrogen halides, ammonium halides and organic halides.

9. The process of claim 8 wherein the vapor is selected from the group consisting of HCl, NH$_4$Cl and organic chlorides.

10. The process of claim 8 wherein the vapor is selected from the group consisting of HBr, NH$_4$Br and organic bromides.

11. The process of claim 7 wherein a halogen compound is added to the olefin feed during the skeletal isomerization in an amount sufficent to maintain catalyst activity.

12. The process of claim 1 wherein a halogen compound is added to the olefin feed during the skeletal isomerization in an amount sufficent to maintain catalyst activity.

* * * * *